United States Patent
Rath et al.

(10) Patent No.: US 9,839,215 B2
(45) Date of Patent: *Dec. 12, 2017

(54) METHODS FOR INCREASING OIL PALM YIELD

(71) Applicant: Valent BioSciences Corporation, Libertyville, IL (US)

(72) Inventors: Andrew Rath, Underwood (AU); Peter D. Petracek, Grayslake, IL (US); Johnny Lopez, Artesia, NM (US); Max G. Villalobos Acuna, Alajuela (CR); Gregory D. Venburg, Deerfield, IL (US); Warren E. Shafer, Libertyville, IL (US)

(73) Assignee: VALENT BIOSCIENCES CORPORATION, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/259,185

(22) Filed: Sep. 8, 2016

(65) Prior Publication Data

US 2017/0064948 A1 Mar. 9, 2017

Related U.S. Application Data

(60) Provisional application No. 62/215,695, filed on Sep. 8, 2015.

(51) Int. Cl.
*A01N 37/10* (2006.01)
*A01N 37/44* (2006.01)

(52) U.S. Cl.
CPC .............. *A01N 37/10* (2013.01); *A01N 37/44* (2013.01)

(58) Field of Classification Search
CPC ................................ A01N 37/10; A01N 37/44
See application file for complete search history.

(56) References Cited

U.S. PATENT DOCUMENTS

| | | | | |
|---|---|---|---|---|
| 2007/0265166 | A1* | 11/2007 | Bardella | ............... A01N 27/00 504/357 |
| 2010/0216641 | A1 | 8/2010 | Wang et al. | |
| 2015/0216136 | A1 | 8/2015 | Yunus et al. | |

FOREIGN PATENT DOCUMENTS

GB    1209743    10/1970

OTHER PUBLICATIONS

Yuan, R., Effects of NAA, AVG, and 1-MCP on Ethylene Biosynthesis, Preharvest Fruit Drop, Fruit Maturity, and Quality of 'Golden Supreme' and 'Golden Delicious' Apples, 2007, HortScience, vol. 42, Issue 1, pp. 101-105.*
Nizam, K., The Effects of Potent Plant Growth Regulators (PGRs) on in vitro Flowering of Oil Palm, 2012, Proceedings of the 7th IMG-GT UNINET and the 3rd International PSU-UNS Conferences on Bioscience, pp. 97-101.*
Termizi, Z., The Effects of Different Concentrations of NAA on Oil Palm (Elaeis guineensis) Embryoid Cultures and Phytosterols Production, 2014, Australian Journal of Crop Science, vol. 8, Issue 6, pp. 840-847.*
International Search Report and Written Opinion issued by the International Bureau in corresponding application No. PCT/US2016/050634 dated Nov. 17, 2016.
UNEP Global Environmental Alert Service (GEAS) "Oil palm plantations: threats and opportunities for tropical ecosystems", Dec. 2011.
Chan et al., "Effects of growth regulators on fruit abscission in oil palm, Elaeis guineensis" Ann. appl. Biol. (1972), 71, pp. 243-249.
Olien et al., "The effect of ethephon-induced gum accumulation in sour cherry (Prunus Cerasus L.) on shoot water relations and hydraulic conductance", Acta Horticulturae 137, 1983 Growth Regulators, pp. 55-64.
Tranbarger et al., "Regulatory mechanisms underlying oil palm fruit mesocarp maturation, ripening, and functional specialization in lipid and carotenoid metabolism", Plant Physiology, Jun. 2011, vol. 156, pp. 564-584.
Silverman et al., "Aminoethoxyvinylglycine effects on late-season apple fruit maturation", Plant Growth Regulation 43; 2004, pp. 153-161.
Retamales et al., "AVG and fruit set: a tool for which novel applications are still being developed in various fruit crops—the case of walnuts", Proc XIth Is on Plant Bioregulators in Fruit Production Ed.: G. Costa Acta Hort. 884, ISHS 2010, pp. 337-342.
Nufarm Limited, "ReTain" 2012 product information, 2 pp.

* cited by examiner

Primary Examiner — John Pak
Assistant Examiner — Andriae M Holt
(74) Attorney, Agent, or Firm — Wood, Phillips, Katz, Clark & Mortimer

(57) ABSTRACT

The present invention is directed to methods of using 1-naphthaleneacetic acid (NAA), or a salt thereof, alone or in combination with aminoethoxyvinylglycine (AVG), or a salt thereof, on oil palm before harvest to increase oil production.

8 Claims, No Drawings

METHODS FOR INCREASING OIL PALM YIELD

CROSS-REFERENCE TO RELATED APPLICATION

This application claims priority of U.S. Provisional Application 62/215,695 filed Sep. 8, 2015, the disclosure of which is incorporated herein by reference.

FIELD OF THE INVENTION

The present invention is directed to methods of using 1-naphthaleneacetic acid (NAA), and salts thereof, on oil palm prior to harvest to increase oil production.

BACKGROUND OF THE INVENTION

Oil palms (*Elaeis guineensis, Elaeis oleifera*, or a cross thereof) are palms that are grown to produce oil. Oil palms grow up to 20 meters tall. Their fruit is reddish in color and about the size of a plum. The fruits grow in large bunches which grow around the palm. The time from pollination of the flowers to maturation of the fruit is about five to six months. Oil palms produce bunches year-round and the fruits are harvested as they reach maturity.

The oil palm's fruit consists of a fleshy outer layer that surrounds a palm kernel. Oil is extracted from the pulp of the fleshy outer layer and from the kernel. Oil palm is an important crop for vegetable oil production and is grown on about 15 million hectares worldwide (UNEP Global Environmental Alert Service, December 2011). The demand for palm oil is expected to double by 2020.

To meet the increasing demand for palm oil and improve efficiency, agronomic methods such as tree spacing, increased planting, fertilization, and irrigation as well as genetic improvement have been developed to optimize oil production (Corley, R. H. V. and P. B. Tinker, 2003, The Oil Palm, 4$^{th}$ edition, New York, John Wiley and Sons, 590 pp). There is still a need, however, for methods to increase production of currently planted oil palms. There is also still a need to maximize the oil production of plants produced through genetic improvement. Further, there is a need to increase oil production of the palms managed by spacing, increased planting, fertilization, and irrigation.

Ethylene is a two carbon gaseous hydrocarbon molecule that acts as a regulator of plant growth and development. Ethylene plays important roles in many physiological processes through the lifecycle of plants including the promotion of germination, reduction of early plant growth, increase in male flower number, abscission of flowers and fruit, and promotion of ripening (Abeles, F. A., P. W. Morgan and M. E. Saltveit, 1992, Ethylene in Plant Biology, 414 pp).

The effect of ethylene on the oil content of oil palm fruit is not well understood, however, the available literature suggests that application of ethylene increases oil content. For example, Chan, et al. (1972, Ann. Appl. Biol. 71: 243-249) showed that preharvest application of the ethylene-releasing agent ethephon (2-chloroethyl phosphonic acid) to attached bunches of oil palm fruit increased oil content by 7%. Tranbarger, et al. (2011, Plant Physiol. 156: 564-584) found concomitant increase in preharvest oil content and the ethylene level generated endogenously in the oil palm fruit. These reports suggest a relationship between increased ethylene levels and increased palm oil content.

Despite showing promise as a way to increase oil content, ethylene has numerous negative effects on plants which are well known in plant physiology. For example, ethylene promotes abscission of fruits and flowers which would decrease yield and yield potential (Abeles, F. A., P. W. Morgan and M. E. Saltveit, 1992, Ethylene in Plant Biology, 414 pp). In fruit trees and bulbs, ethylene can cause the physiological disease gummosis (Olien, W. C. and M. J. Bukovac, 1983, Acta Hort. 137: 55-64). Gummosis is a generalized disorder of trees in which polysaccharide gum is overproduced, exuded, and deposited on the bark. Gummosis affects water relations, promotes disease, is attractive to wood-boring insects, causes shoot death, and leads to early tree decline. Based on these effects, application (particularly repeated application) of ethylene may not provide an overall benefit in oil palm.

Accordingly, there is a need for practical methods to increase the amount of oil that oil palm trees produce. These methods should produce more oil while not harming the oil palm and should be easy to apply to the fruit or oil palm.

SUMMARY OF THE INVENTION

In one aspect, the invention is directed to methods of increasing the content of oil in oil palm fruits by application of NAA, or a salt thereof, to the oil palm fruit before the oil palm fruit is harvested.

In another aspect, the invention is directed to methods of increasing the content of oil in oil palm fruits by application of NAA, or a salt thereof, and aminoethoxyvinylglycine (AVG), or a salt thereof, to the oil palm fruit before the oil palm fruit is harvested.

DETAILED DESCRIPTION OF THE INVENTION

NAA is a synthetic auxin plant hormone. It is known to stimulate root growth.

AVG ([S]-trans-2-amino-4-(2-aminoethoxy)-3-butenoic acid, aminoethoxyvinylglycine, aviglycine) is a known ethylene antagonist. AVG formulations (such as those available from ValentBioSciences Corporation, Libertyville, Ill.) have been shown to inhibit fruit drop and retain stone fruit and apple fruit quality (Silverman, et al., 2004. Plant Growth Reg. 43:153-161), increase cherry and walnut fruit set (Retamales and Petracek, 2010. Acta Hort. 884:337-341), and increase male flower number in cucurbits.

Applicant unexpectedly found that NAA increases the oil yield of oil palms when NAA is applied before harvest of the fruit. This finding was unexpected because auxins are not known to increase oil yields. This was also unexpected because other plant growth regulators, such as 6-benzyladenine, failed to increase oil yield. Further, the plant growth regulator gibberellic acid provided inconsistent and unsatisfactory oil yields.

Applicant also unexpectedly found that the combination of NAA and AVG increases the oil yield of oil palms when NAA and AVG are applied before harvest of the fruit. This was unexpected because the literature shows that ethylene increases oil in oil palm when applied before harvest. This suggests that application of the ethylene antagonist AVG would have the opposite effect as ethylene on the oil content of oil palm. Applicant, however, found that the amount of oil increased when NAA and AVG were applied before harvest to the fruits.

In one embodiment, the invention is directed to methods for increasing oil content of oil palm fruit comprising applying NAA, or a salt thereof, to oil palm fruit before the oil palm fruit is harvested.

The timing of application of NAA, or a salt thereof, to the bunches of fruit is after formation of the bunches. This timing does not include when the oil palm is a seedling. Preferably, the timing range is from initial flowering to prior to harvest. More preferably, the timing range is from just prior to initial fruit drop through early fruit drop from the most mature bunch or bunches on the oil palm. This timing corresponds to about 3 to 4 weeks before harvest to the day of harvest. Most preferably, the timing corresponds to 1 to 2 weeks before harvest to the day of harvest.

Preferably, the concentration of NAA, or a salt thereof, that is applied to the plant is from about 1 to about 1,000 ppm. The more preferred concentration is from about 50 to about 500 ppm. The most preferred concentration is from about 100 to about 300 ppm.

Preferably, the volume of the application of NAA, or a salt thereof, is from about 20 to about 2,000 ml per palm plant. The most preferred volume of application is from about 50 to about 600 ml per palm plant.

Preferably, the NAA, or a salt thereof, dose is from about 0.01 g to about 1 g per palm per application. The more preferred NAA, or a salt thereof, dose is from about 0.05 g to about 0.5 g per palm per application. The most preferred NAA, or a salt thereof, dose is from about 0.1 g to about 0.3 g per palm per application.

The preferred interval of application of NAA, or a salt thereof, is from about every 7 to about every 21 days. The most preferred interval of application is from about every 10 to about every 14 days.

Suitable NAA salts include, but are not limited to, the ammonium salt, the lithium, sodium, potassium, magnesium, or calcium salts, organic amine salts or mixtures comprising any number of these. In one embodiment, the organic amine salt is the triethanolamine salt. In another embodiment, the organic amine salt is the dimethylethanolamine salt. In yet another embodiment, the organic amine salt is the ethanolamine salt. These examples of salts are not limiting as other salts may also be suitable for use the present invention.

Adjuvants such as surfactants, humectants, stickers, spreaders, urea, oils, and salts may be incorporated in a composition containing NAA to improve performance.

NAA, or a salt thereof, or a composition comprising NAA, or a salt thereof, may be foliar applied to aerial parts of the oil palm including bunches and fronds by methods such as backpack sprayers, mist blowers, extended wand sprayers, tractor or ATV-mounted or UTV-mounted sprayers or aerial application by fixed wing, helicopter, or drone aircraft. The most preferred foliar application is targeted to the oldest bunches of fruits on the palm. NAA, or a salt thereof, or a composition comprising NAA, or a salt thereof, may be applied to the ground by drip irrigation or fertigation with nutrients or applied by trunk or bunch injection.

In another embodiment, the invention is directed to methods for increasing oil content of oil palm fruit comprising applying NAA, or a salt thereof, and AVG, or a salt thereof, to oil palm fruit before the oil palm fruit is harvested.

The timing of application of NAA, or a salt thereof, and AVG, or salt thereof, to the bunches of fruit is after formation of the bunches. This timing does not include when the oil palm is a seedling. Preferably, the timing range is from initial flowering to prior to harvest. More preferably, the timing range is from just prior to initial fruit drop through early fruit drop from the most mature bunch or bunches on the oil palm. This timing corresponds to about 3 to 4 weeks before harvest to the day of harvest. Most preferably, the timing corresponds to 1 to 2 weeks before harvest to the day of harvest.

Preferably, the concentration of NAA, or a salt thereof, that is applied to the plant with AVG, or a salt thereof, is from about 1 to about 10,000 ppm. The more preferred concentration is from about 20 to about 2,000 ppm. The most preferred concentration is from about 100 to about 300 ppm.

Preferably, the NAA, or a salt thereof, dose when applied with AVG, or a salt thereof, is from about 0.01 g to about 1 g per palm per application. The more preferred NAA, or a salt thereof, dose is from about 0.05 g to about 0.5 g per palm per application. The most preferred NAA, or a salt thereof, dose is from about 0.1 g to about 0.3 g per palm per application.

In a preferred embodiment, the AVG salt is AVG-HCl.

Preferably, the concentration of AVG, or a salt thereof, that is applied to the plant with NAA, or a salt thereof, is from about 1 to about 10,000 ppm. The more preferred concentration is from about 20 to about 2,000 ppm. The most preferred concentration is from about 100 to about 500 ppm.

Preferably, the volume of the application of NAA and AVG, or salts thereof, is from about 20 to about 2,000 ml per palm plant. The most preferred volume of application is from about 50 to about 600 ml per palm plant.

Preferably, the AVG, or a salt thereof, dose when applied with NAA, or a salt thereof, is from about 0.02 mg to about 20 g per palm per application. The more preferred AVG, or a salt thereof, dose when applied with NAA, or a salt thereof, is from about 0.4 mg to about 4,000 mg per palm per application. The most preferred AVG, or a salt thereof, dose when applied with NAA, or a salt thereof, is from about 10 mg to about 300 mg per palm per application.

The preferred interval of application of NAA and AVG, or salts thereof, is from about every 7 to about every 21 days. The most preferred interval of application of NAA and AVG, or salts thereof, is from about every 10 to about every 14 days.

Adjuvants such as surfactants, humectants, stickers, spreaders, urea, oils, and salts may be incorporated in a composition containing NAA and AVG, or salts thereof, to improve performance.

NAA and AVG, or salts thereof, or a composition comprising NAA and AVG, or salts thereof, may be foliar applied to aerial parts of the oil palm including bunches and fronds by methods such as backpack sprayers, mist blowers, extended wand sprayers, tractor or ATV-mounted or UTV-mounted sprayers or aerial application by fixed wing, helicopter, or drone aircraft. The most preferred foliar application is targeted to the oldest bunches of fruits on the palm. NAA and AVG, or salts thereof, or a composition comprising NAA and AVG, or salts thereof, may be applied to the ground by drip irrigation or fertigation with nutrients or applied by trunk or bunch injection.

As used herein, "yield" refers to the amount of oil that is produced from the oil palm.

As used herein, "prior to harvest," "before harvest," and "preharvest" all refer to a time before the most mature bunches and their fruits are harvested from the oil palm.

Throughout the application, the singular forms "a," "an," and "the" include plural reference unless the context clearly dictates otherwise.

As used herein, all numerical values relating to amounts, weight percentages and the like are defined as "about" or "approximately" each particular value, plus or minus 10%.

For example, the phrase "at least 5.0% by weight" is to be understood as "at least 4.5% to 5.5% by weight." Therefore, amounts within 10% of the claimed values are encompassed by the scope of the claims.

These representative embodiments are in no way limiting and are described solely to illustrate some aspects of the invention.

The invention is demonstrated by following representative examples. The following examples are offered by way of illustration only and not by way of limitation.

EXAMPLES

Example 1

Plant Material: A field study was executed in a plantation in Costa Rica to compare the effects of one-time bunch-directed applications of: (1) water sprayed untreated control (UTC); (2) AVG-HCl at 500 ppm (59.5 g) active ingredient (a.i.); (3) AVG-HCl at 125 ppm (14.9 g) a.i.; (4) 200 ppm (0.2 g) a.i. of NAA; (5) AVG-HCl at 500 ppm (59.5 g) a.i. and 200 ppm (0.2 g) a.i. of NAA; and (6) AVG-HCl at 125 ppm (14.9 g) a.i. and 200 ppm (0.2 g) a.i. of NAA. In this study, AVG was provided in a formulation as AVG-HCl. NAA was provided as the sodium salt at concentrations of 20% and 3.5%. For each treatment, 24 palms per treatment were randomly selected covering about 15 hectares. The palms were Compact×Ghana plants and 2.5 to 3 years old.

Treatment Application: A manual DEA-2000 sprayer was used to spray all treatments (100 mL/bunch) to bunches with 1 to 3 loose fruits.

The time required to spray each bunch was about 11 to 20 seconds depending on the sprayer. Sprays were conducted only once per bunch. Twelve bunches were sprayed on Oct. 28, 2014 and the other 12 on Nov. 4, 2014.

Cumulative loose fruit (CLF) and cumulative loose mass (CLM) counts were determined at daily basis with exception of Sundays for 14 days in order to objectively quantify fruit abscission. An electronic balance was used to weight out all fruit. All loose fruit on the bunch, branches and on the ground was counted and weighed.

Results: Table 1 below shows the effects on CLF and CLM of NAA, AVG, and combinations thereof, on oil palm.

TABLE 1

| Treatment | Cumulative Loose Fruit | % Difference with UTC | Cumulative Loose Mass (g) | % Difference with UTC |
|---|---|---|---|---|
| 1 UTC | 167.2 | n/a | 1924 | n/a |
| 2 500 ppm (59.5 g) AVG | 86.1 | 48.5 | 1154 | 40.0 |
| 3 125 ppm (14.9 g) AVG | 160.7 | 3.9 | 2028 | −5.4 |
| 4 200 ppm (0.2 g) NAA | 114.8 | 31.3 | 1501 | 22.0 |
| 5 500 ppm (59.5 g) AVG + 200 ppm (0.2 g) NAA | 63.2 | 62.2 | 779 | 59.5 |
| 6 125 ppm (14.9 g) AVG + 200 ppm (0.2 g) NAA | 99.6 | 40.4 | 1319 | 31.4 |

As seen in Table 1, NAA reduced CLF 31.3 percent relative to the UTC and also improved the effect of AVG. One hundred twenty-five ppm AVG reduced CLF 3.9 percent while the same treatment combined with NAA reduced CLF 40.4 percent. Five hundred ppm AVG alone reduced CLF 48.5 percent while the same rate combined with NAA reduced CLF 62.2 percent.

NAA reduced CLM 22 percent relative to the UTC and also improved the effect of AVG. One hundred twenty-five ppm AVG increased CLF 5.4 percent while the same treatment combined with NAA reduced CLF 31.4 percent. Five hundred ppm AVG alone reduced CLF 40 percent while the same rate combined with NAA reduced CLF 59.5 percent.

Fewer loose fruits and less loose mass are desirable because it means that the fruit will spend more time on the tree producing oil. Accordingly, it was determined that NAA treatments, alone or in combination with AVG, would provide increased oil yield compared to untreated plants.

We claim:

1. A method of increasing oil content of oil palm fruit comprising applying an effective amount of a composition consisting of the combination of 1-naphthaleneacetic acid (NAA), or a salt thereof, and aminoethoxyvinylglycine (AVG), or a salt thereof and at least one adjuvant selected from the group consisting of surfactants, humectants, stickers, spreaders, urea, oils, and a liquid carrier, to oil palm fruit before the oil palm fruit is harvested, wherein the effective amount is from about 0.05 g to about 0.5 g of NAA per palm per application and from about 0.02 mg to about 20 g of AVG per palm per application.

2. The method of claim 1 wherein the NAA, or a salt thereof, and the AVG, or a salt thereof, are applied from about three weeks before the fruit is harvested to about the day before the fruit is harvested.

3. The method of claim 1 wherein from about 0.1 g to about 0.3 g of NAA is applied to the oil palm.

4. The method of claim 1 wherein the NAA and AVG are applied from about every 7 to about 21 days.

5. The method of claim 4 wherein the NAA and AVG applied from about every 10 to about 14 days.

6. The method of claim 1 wherein from about 0.4 mg to about 4,000 mg of AVG is applied to the oil palm.

7. The method of claim 6 wherein from about 10 mg to about 300 mg of AVG is applied to the oil palm.

8. The method of claim 1 wherein the salt of AVG is AVG-HCl.

* * * * *